(12) United States Patent
Arbogast et al.

(10) Patent No.: US 6,797,008 B1
(45) Date of Patent: Sep. 28, 2004

(54) SYSTEM AND METHOD FOR SECURING A PROSTHETIC LIMB

(75) Inventors: Robert E. Arbogast, Mt. Sterling, OH (US); James W. Capper, Mt. Sterling, OH (US); James M. Colvin, Hilliard, OH (US)

(73) Assignee: Ohio Willow Wood, Mt. Sterling, OH (US)

( * ) Notice: Subject to any disclaimer, the term of this patent is extended or adjusted under 35 U.S.C. 154(b) by 0 days.

(21) Appl. No.: 10/033,064

(22) Filed: Oct. 22, 2001

(51) Int. Cl.[7] .................................................. A61F 2/80
(52) U.S. Cl. ........................................... 623/34; 623/36
(58) Field of Search ..................................... 623/32–37

(56) References Cited

U.S. PATENT DOCUMENTS

| | | | | |
|---|---|---|---|---|
| 2,834,025 | A | * 5/1958 | Leavy ........................... | 623/33 |
| 4,923,474 | A | * 5/1990 | Klasson et al. ................ | 623/33 |
| 5,326,351 | A | * 7/1994 | Sarazin ......................... | 623/33 |
| 5,368,281 | A | 11/1994 | Skyba ........................... | 254/391 |
| 5,722,640 | A | 3/1998 | Skyba ........................... | 254/333 |
| 6,149,133 | A | 11/2000 | Skyba ........................... | 254/391 |
| 6,267,787 | B1 | 7/2001 | Capper et al. ................. | 623/36 |
| 2002/0042659 | A1 * | 4/2002 | Ingimarsson .................. | 623/33 |
| 2002/0077705 | A1 * | 6/2002 | Perkins et al. ................ | 623/36 |

FOREIGN PATENT DOCUMENTS

| DE | 1 082 702 | * 6/1960 | .................. 623/34 |
|---|---|---|---|
| DE | 195 31 070 A1 | * 2/1997 | ............. A61F/2/78 |

OTHER PUBLICATIONS

OSSUR, product specification sheet of a lanyard system (date unknown). Icelock™ lanyard 331–L; L–331001 (2 pages).
Website and product information pertaining to Icelock 600 Series, http://www.ossur.com/template13.asp?PageID+334, dated Oct. 26, 2001, three pages.

* cited by examiner

Primary Examiner—David H. Willse
(74) Attorney, Agent, or Firm—Standley Law Group LLP

(57) ABSTRACT

A system and method for releasably securing a prosthetic limb to a residual limb. The system and method utilizes a lanyard for drawing the residual limb into a receiving portion of the prosthetic limb and for helping to maintain attachment of the prosthetic limb to the residual limb. The lanyard is routed through a releasable ratchet mechanism, which allows tension to be incrementally applied to the lanyard and further prevents the lanyard and the residual limb connected thereto from moving in an opposite direction. A suction cup may also be employed within the receiving portion of the prosthetic limb for aiding in retention of the residual limb. The ratchet mechanism allows the system to be used without maintaining constant tension on the lanyard, thereby reducing the amount of effort required of the user. The system and method also reduces or even eliminates pistoning of the residual limb within the prosthetic limb during movement of the user.

32 Claims, 6 Drawing Sheets

SYSTEM AND METHOD FOR SECURING A PROSTHETIC LIMB

BACKGROUND AND SUMMARY OF THE INVENTION

The present invention relates to a method and apparatus for securing a prosthetic limb to the residual limb of an amputee. More specifically, the method and apparatus of the present invention allows an amputee to easily and accurately secure a prosthetic limb to their own residual limb, in a manner that reduces or even eliminates the pistoning movement that may commonly occur therebetween.

While prosthetic limbs have been around in some form for many years, there are still certain difficulties associated with properly affixing a prosthetic limb to the residual limb of an amputee. These difficulties are typically compounded when the prosthetic limb replaces a portion of an amputee's leg and, therefore, must be able to support the weight of the amputee and remain secured to the residual leg while allowing the amputee to be ambulatory. There are numerous known techniques for securing a prosthetic leg to a residual leg, many of which are described in detail below.

Early prosthetic legs were often equipped with an apparatus having a belt strap(s) that extended from the top of the prosthetic leg. The belt strap(s) was designed to engage a belt worn around the amputee's waist. Thus, once the prosthetic leg was in place, the belt strap(s) could be pulled tight and secured to the waist belt. This method did not, however, provide satisfactory results, as the apparatus proved to be quite cumbersome, and a loosening of the prosthetic leg often occurred due to slippage of the belt strap(s) or a sagging of the belt around the amputee's waist.

Systems have also been developed that allow the residual leg of an amputee to be secured within a receiving cavity of a prosthetic leg via suction created therebetween. It is possible to design such a system so that a very secure initial fit can be accomplished. The drawback to a pure suction system, however, is that any fluctuations in the size of the residual leg can cause a loss of suction, thereby resulting in a less secure fit between the limbs. This has proven to be a common problem with such systems, as the residual leg may often shrink or swell throughout the day as the amputee engages in physical activity. Also problematic is the fact that a residual limb may change shape from day to day for a variety of reasons.

There also exist specialized socks or liners that fit tightly over a residual leg and are adapted to engage with a corresponding prosthetic leg. In one such liner, a cup having a downward protruding pin or screw is provided in the bottom portion thereof. The amputee places the liner on the residual leg and inserts the residual leg into a receiving portion of a prosthetic leg. As the residual leg becomes seated in the prosthetic leg, the pin or screw engages a receiving aperture therein. The aperture may allow the liner to be secured to the prosthetic leg by, for example, threading thereto, or by an interlocking arrangement.

In another version of a liner securing system, a prosthetic leg may have a lanyard passing through the bottom of a residual leg receiving portion thereof. The lanyard may have a threaded element or some other attachment means affixed to one end, so that the lanyard may be releasably connected to a bottom portion of a liner, such as to a cap or cup. In this system, the liner is placed over the residual leg, and the lanyard is attached thereto. As the residual leg is inserted into the prosthetic leg, the segment of the lanyard that extends outside the prosthetic limb can be pulled on by the amputee to assist in ensuring full insertion of the residual leg into the prosthetic leg. Once the residual limb is fully inserted into the prosthetic leg, tension may be maintained on the lanyard and the lanyard may be secured to a belaying cleat or similar retaining device located on the prosthetic limb. The tension of the lanyard against the bottom of the liner then aids in maintaining the position of the residual leg within the prosthetic leg.

As can be seen, there have been numerous attempts at providing a system for securely retaining the residual leg of an amputee within a prosthetic leg. Each of these known systems has drawbacks or deficiencies, however. For example, the security provided by the belt strap and waist belt system is inadequate and has proven uncomfortable to the wearer thereof. As previously mentioned, any changes in the size of the residual leg can have adverse effects on a suction system, as such a system relies on a very close fit between the residual leg and prosthetic leg to maintain a vacuum therebetween. Suction systems also are problematic, in that somewhat embarrassing sounds may be generated thereby both during insertion of the residual leg into the prosthetic leg and during movement of the amputee. These sounds are typically created as small amounts of trapped air escape through gaps between the residual leg and the prosthetic leg. Each of the presently known liner securing systems are also inadequate. The former liner system requires that a securing pin or screw on the bottom of the liner be guided into an engaging feature in the bottom of the receiving cavity of the prosthetic leg. This must be accomplished without the ability to see the engaging feature or the securing pin or screw, as insertion of the residual leg into the prosthetic leg blocks the view of each. The latter liner securing system requires that the amputee have significant hand/arm strength in order to pull the lanyard taut and to maintain the tautness as the lanyard is secured to the belaying cleat. Any slack that develops in the lanyard during this process will result in a less than adequate securing of the residual leg to the prosthetic leg. Such a process can be quite difficult, especially for an elderly and/or arthritic person who lacks the requisite hand/arm strength.

One consequence that results from the inability of the above-described systems to adequately secure a residual limb to a prosthetic limb is that at least a small amount of movement commonly occurs therebetween. In the context of its occurrence between a residual and prosthetic leg, this movement is commonly referred to as "pistoning." Although such pistoning may only involve movement of the residual leg within the prosthetic leg on the order of fractions of an inch, it is nonetheless uncomfortable for the user, and may further impart a feeling of instability. Further, friction caused by this pistoning commonly wears away the material of the liner that is typically placed over the residual leg—the result being that the liner must be discarded.

From the foregoing description of the known systems, it can be seen that there is a need for a system and method for easily and adequately securing a residual limb to a prosthetic limb. The system and method of the present invention satisfies this need. The system and method of the present invention allows an amputee to easily fit a prosthetic limb to their residual limb and to securely affix the prosthetic limb thereto. While the system and method of the present invention can be applied to a variety of artificial limbs, for purposes of illustration the system and method will be described herein only with respect to its application to a prosthetic leg.

One exemplary embodiment of the system and method of the present invention described herein, utilizes a lanyard that passes through substantially the bottom of a receiving cavity of a prosthetic leg to secure an amputee's residual leg thereto. A liner is placed over the residual leg before the residual leg is inserted into the prosthetic leg. The liner is preferably provided with a specialized bottom portion that is designed to engage a receiving device located in the receiving cavity, and is further adapted for attachment to one end of the lanyard. Prior to entering the bottom of the receiving cavity, the lanyard travels through a ratchet mechanism that is located between the receiving cavity portion of the prosthetic leg and the lower portion of the prosthetic leg. When installing the prosthetic leg, the amputee releasably connects the coupling element to the liner prior to inserting the residual leg into the receiving cavity. During this time, the ratchet mechanism is set to allow the free movement of the lanyard therethrough, or is otherwise set to allow ratcheting of the lanyard toward the liner. After connection of the lanyard to the liner, the ratchet mechanism is set to the engaged, or ratcheting (tightening) position, whereby the lanyard may only travel therethrough in a direction that encourages the insertion of the residual leg into the receiving cavity. A suction cup may provided as part of the receiving device that is located in the receiving cavity to accept the distal end of the residual leg. The lanyard may be withdrawn from the receiving cavity by the amputee such that distal end of the residual leg is pulled into secure abutment with the suction cup. The position of the residual leg within the prosthetic leg is then positively retained by the tension of the lanyard, which tension is maintained by the ratchet mechanism.

The system and method of the present invention provides for an easier and more secure installation of the prosthetic leg to the residual leg than is possible with known systems. The ratchet mechanism allows the lanyard to be withdrawn in small increments if desired, without having to maintain a tensile force on the lanyard. The increments are generally detectable by both feel and sound. Because the ratchet mechanism prevents the lanyard from being drawn back into the receiving cavity, the position of the lanyard can be maintained even if the end thereof is released by the amputee. Continuous tension on the lanyard by the amputee is not required, and it is also not necessary that tension be maintained thereon while the lanyard is fastened to a securing feature on the prosthetic leg, such as a belaying cleat. Thus, the ratchet mechanism allows the residual leg to be drawn into the prosthetic leg and secured thereto even if the amputee lacks the hand/arm strength necessary to use a known lanyard securing system.

The ratchet mechanism of the present invention also provides for a more secure fit of the residual leg with the prosthetic leg than has been heretofore possible. Because the ratchet mechanism will not allow the lanyard to be drawn back into the receiving cavity of the prosthetic leg, the position of the prosthetic leg is better maintained during the ambulatory activities of the amputee. Further, the ratchet mechanism eliminates the need for the amputee to maintain tension on the lanyard while securing the lanyard to the prosthetic leg—thereby reducing the possibility of an insecure fit due to the amputee allowing the lanyard to slacken during the securing thereof. As a result of using the system and method of the present invention, the above-described pistoning of the residual leg can be reduced or even eliminated. Further details regarding the system and method of the present invention can be ascertained by observation of the following drawing figures and detailed description.

BRIEF DESCRIPTION OF THE DRAWINGS

In addition to the features mentioned above, other aspects of the present invention will be readily apparent from the following descriptions of the drawings and exemplary embodiments, wherein like reference numerals across the several views refer to identical or equivalent features, and wherein.

DETAILED DESCRIPTION OF THE EXEMPLARY EMBODIMENT(S)

Figure 1:
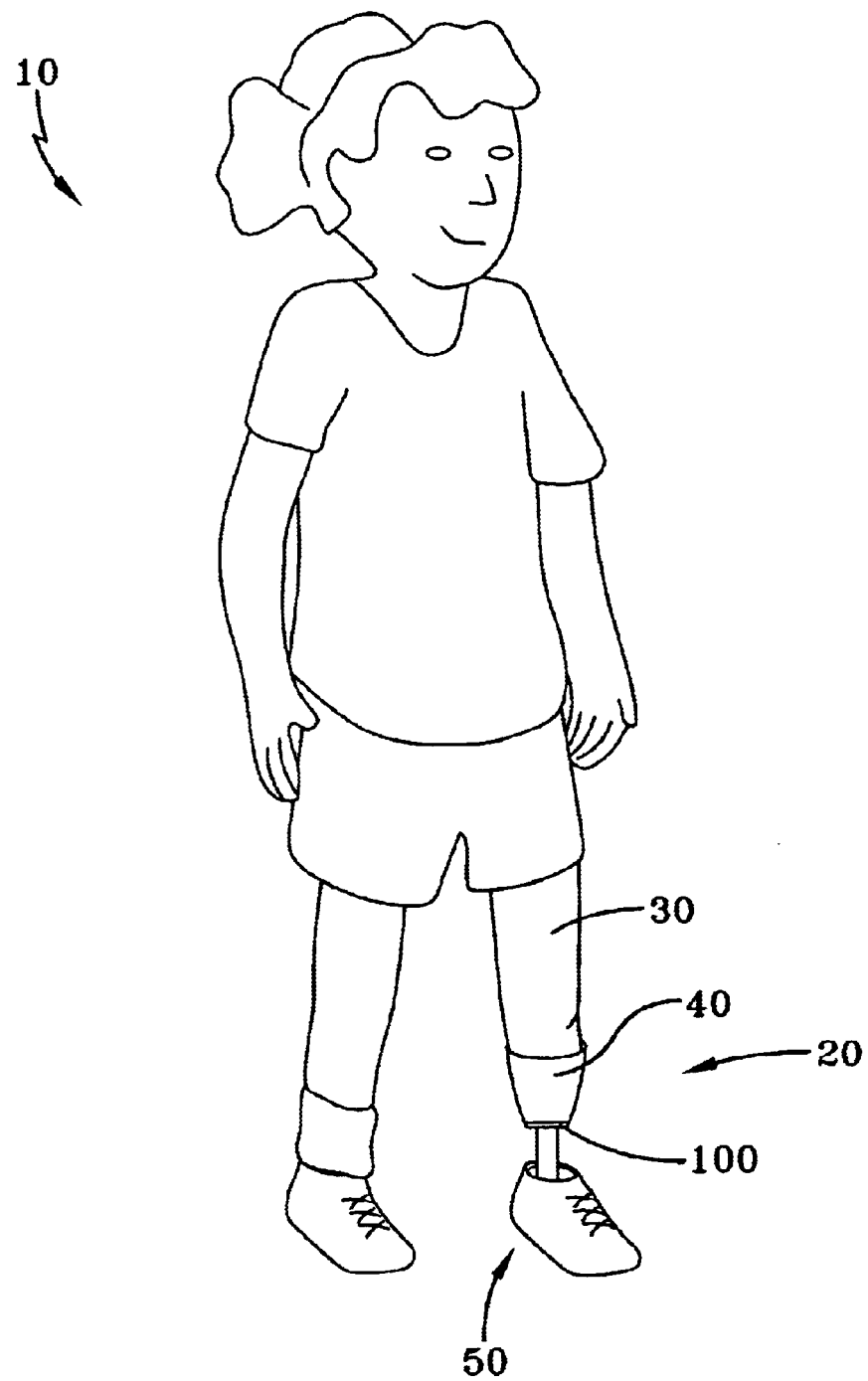
FIG. 1 depicts an amputee after using an embodiment of the system and method of the present invention to secure a prosthetic leg to the amputee's residual leg.

A general view of an amputee 10 having a prosthetic leg 20 can be observed in FIG. 1. In this particular example, the amputee 10 is shown to have a residual leg 30 that stops at a point below the knee—although the term "residual leg" is defined herein to mean that portion of the amputee's natural leg left intact after the amputation process, and may stop either above or below the knee. The prosthetic leg 20 is releasably affixed to the residual leg 30 using one embodiment of the system and method of the present invention. The prosthetic leg 20 is shown to have an upper portion 40, which substantially simulates a calf, and a lower portion 50 that acts as an ankle and foot. In other embodiments, wherein the residual leg 30 stops above the knee, the upper portion 40 and the lower portion 50 may be connected by a flexible joint designed to simulate the action of a knee. The prosthetic leg 20 shown in FIG. 1 is for purposes of illustration and not limitation, and it should be realized by one skilled in the art that there are a multitude of prosthetic leg configurations to which the system and method of the present invention may be applied. For example, the residual leg may end below the knee, the prosthetic leg may not simulate the appearance of a natural leg, the prosthetic leg may not bend, or the prosthetic leg may consist substantially of only a foot. It should also be realized that while for purposes of clarity the system and method of the present invention are being described herein with respect to their application to an artificial leg, nothing is meant to prohibit the use thereof with other types of artificial limbs.

Figure 2:
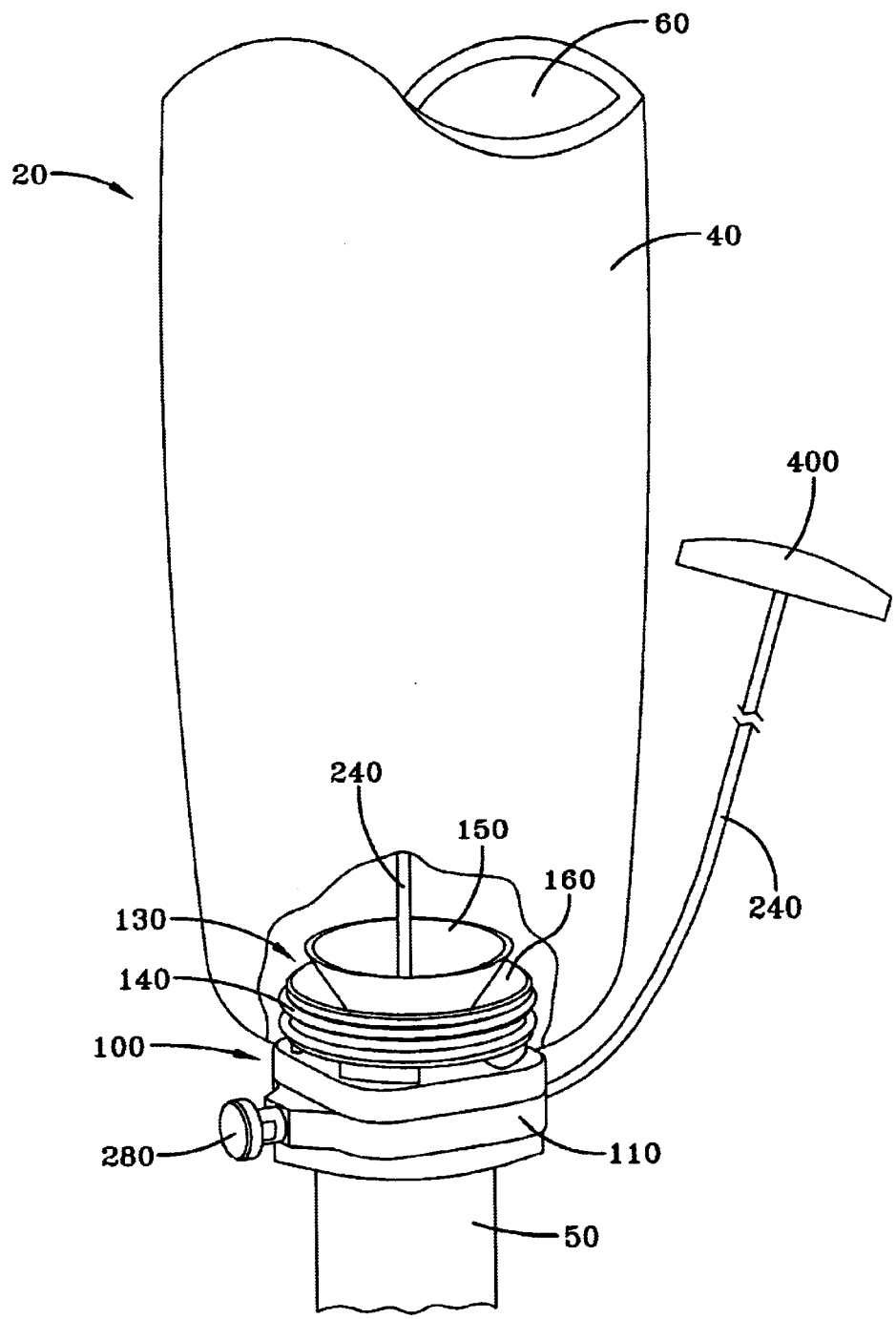
FIG. 2 is an enlarged view, in partial cut-away, illustrating the system of the present invention installed on the prosthetic leg as shown in FIG. 1.
Figure 3:
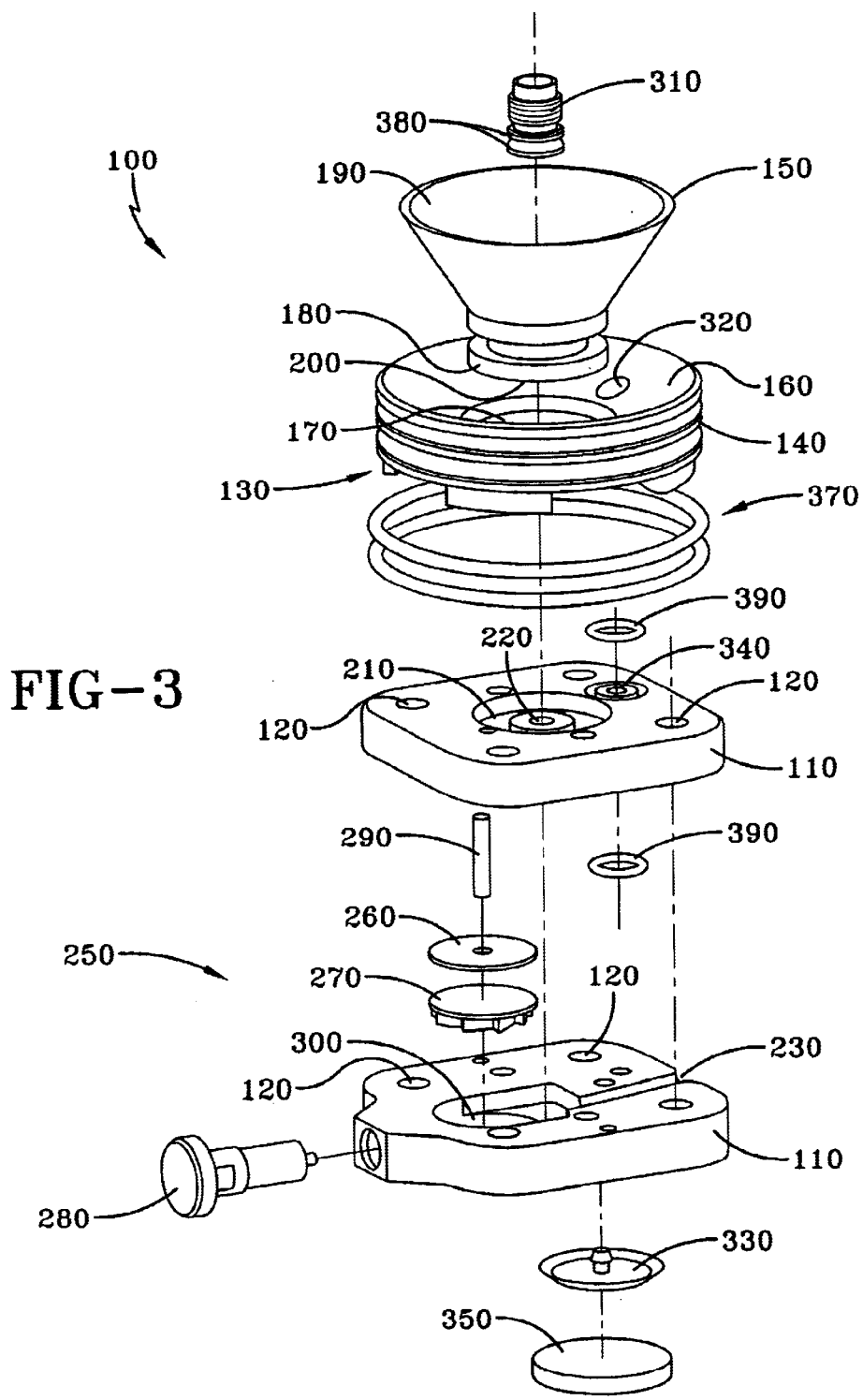
FIG. 3 is an enlarged, exploded view of the components employed in the system and method of the present invention shown in FIGS. 1 and 2.

In the embodiment shown in FIGS. 1–3, the system of the present invention is shown to include a ratchet retention apparatus 100 located between the upper portion 40 and lower portion 50 of the prosthetic leg 20. As can be seen through the cut-away section of the upper portion 40, a structure is located in a receiving cavity 60 of the upper portion of the prosthetic leg 20 to accommodate a distal end of the amputee's residual leg 30 when the residual leg is fully inserted into the prosthetic leg 20. This structure is described in more detail below. It should be understood that the system and method of the present invention is adapted for use with a liner that is placed over the residual leg 30 prior to insertion of the residual leg into the prosthetic leg 20. Such liners are well known in the art and, thus, will not be described in detail herein.

An enlarged, exploded view of the ratchet retention apparatus 100 shown in FIGS. 1–2 can be observed in FIG. 3. It can be seen that the ratchet retention apparatus 100 has a body portion 110. In certain embodiments of the present invention, the body portion will be visible between the upper portion 40 and lower portion 50 of the prosthetic leg 20. In other embodiments of the present invention, the body portion 110 may be located elsewhere. In this particular embodiment, the body portion 110 is adapted for attachment to the upper portion of the prosthetic leg 20. The body portion 110 may be attached to the upper portion 40 of the prosthetic leg 20 by various means. Preferably, threaded fasteners (not shown) pass through apertures 120 in the body portion 110 and through corresponding holes in the bottom of the upper portion 40 of the prosthetic leg 20. The bottom of the upper portion 40 of the prosthetic leg 20 may be reinforced, such as with a metal plate, by lamination, or by other means and materials, in order to provide a sufficient mounting surface for attaching the body portion 110 thereto. The fasteners may also pass through corresponding apertures in the lower portion 50 of the prosthetic leg prior to passing through the body portion 110. In this manner, the lower portion 50 of the prosthetic leg may be secured to the upper portion 40 along with the ratchet retention apparatus 100. Securement of each of the lower portion 50 of the prosthetic leg 20 and the body portion 110, may be accomplished by threading the fasteners into a residual limb receiving device 130 of the ratchet retention apparatus 100 that resides within the receiving cavity 60 of the upper portion 40 of the prosthetic leg. Alternatively, the lower portion 50 of the prosthetic leg 20 and the body portion 110 may be attached to the upper portion by fastening directly to the bottom portion thereof—such as by threading fasteners into a metal plate or reinforced section. In this manner, the bottom of upper portion 40 of the prosthetic leg 20 is trapped between the residual limb receiving device 130 and the body portion 110, and the assembly is secured. In another embodiment, it is also possible that the ratchet retention apparatus 100 may be an integral part of the upper portion. For example, the body portion 110 may be integrated into the upper portion 40 of the prosthetic leg 20 during the forming or molding thereof. Alternatively, the upper portion 40 may be designed to receive the internal components of the ratchet retention apparatus 100, such that the ratcheting operation occurs integrally within the upper portion 40.

In one embodiment of the present invention, the residual limb receiving device 130 consists primarily of a distal adapter 140 and a suction cup 150. The distal adapter 140 is shown to be substantially disk-shaped in this particular embodiment, but other shapes are also possible. Preferably, the top surface 160 of the distal adapter 140 is substantially cup-shaped. The bottom of the distal adapter 140 may be provided with protruding ribs or other features for contacting the bottom of the upper portion 40 of the prosthetic leg 20 and for receiving the fasteners. The distal adapter 140 is provided with a suction cup receiving aperture 170 that extends therethrough at its circumferential axis. A first end 180 of the suction cup 150 is adapted to securely reside within the suction cup receiving aperture 170, such that a seal is formed therebetween. The first end 180 of the suction cup 150 also protrudes through the suction cup receiving aperture 170 and extends downward from the bottom of the distal adapter 140 when the two components are assembled. A second end 190 of the suction cup 150 is designed to receive the liner-covered distal end of the residual leg 30 upon its insertion into the receiving cavity 60. The liner used with the present invention is of the variety having a reinforced cap or cup at the distal end, such that the cap will abut the suction cup 150 when the prosthetic leg 20 is properly seated in the residual leg 30. Preferably, a vacuum is formed between the suction cup 150 and the cap on the liner, which vacuum assists in retaining the residual leg 30 within the prosthetic leg 20. A lanyard aperture 200 also passes axially through the suction cup 150, such that a lanyard passageway is formed through the suction cup and the distal adapter 140 when the components are assembled.

In another embodiment of the present invention, the residual limb receiving device that is located in the receiving cavity 60 and provided to receive the distal end of the residual limb 30 may be integral to the upper portion 40. More specifically, rather than existing as a separate component that must be located in the receiving cavity 60, the residual limb receiving device may be molded or otherwise integrally formed with the upper portion 40. The residual limb receiving device is simply created along with the upper portion 40 and preferably takes into account the size and shape of the residual limb of the amputee who will wear the prosthetic leg.

Referring again specifically to the embodiment of FIG. 3, it can be observed that the top surface of the body portion 110 has a suction cup receiving recess 210 for accepting the portion of the first end 180 of the suction cup 150 that extends downward from the bottom of the distal adapter 140. A lanyard entry aperture 220 and exit aperture 230 are also located in the body portion 110 for allowing the passage therethrough of a lanyard 240. The lanyard 240 may consist of a rope, cord, wire, belt or other similar stay. The lanyard entry aperture 220 is substantially centered within the suction cup receiving recess 210, so that the lanyard 240 may enter the body portion 110 through the distal adapter 140 and suction cup 150 via the lanyard passageway. The lanyard exit aperture 230 is preferably located on a side of the body portion 110. It is also possible, however, for the lanyard exit aperture 230 to be located on the bottom of the body portion 110. The lanyard 240 extends from the lanyard exit aperture 230 for grasping by the amputee 10.

A ratchet mechanism 250 resides within the body portion 110 such that the lanyard 240 is acted upon by the ratchet mechanism as it passes through the body portion. In this embodiment, the ratchet mechanism 250 comprises a pulley 260 having a pawl 270 attached thereto, and a preferably spring-loaded ratchet release element 280 for causing the engagement or release of the ratcheting function. It should be realized, however, that various types of ratchet mechanisms may be employed to achieve the desired result. The pulley 260 is adapted to revolve around a shaft 290 and within a cavity 300 in the body portion 110. As can be seen in FIG. 3, the pathway between the lanyard entry aperture 220 and lanyard exit aperture 230 forces the lanyard 240 into communication with the ratchet mechanism 250. Specifically, the lanyard 240 is caused to wrap around the pulley 260 prior to exiting the ratchet body 110 via the lanyard exit aperture 230. In the case where the ratchet release element 280 is in an engaged position, the lanyard 240 is permitted to travel through the body portion 110 in only a single direction-that being in a direction that causes the lanyard to be withdrawn from the lanyard exit aperture 230. The singular direction of travel is caused by the end of the ratchet release element 280 engaging the teeth of the pawl 270, and the inability of the lanyard 240 to slip through its convoluted path around the pulley 260. In this mode, the lanyard 240 may be withdrawn through the lanyard exit aperture 230 in small, detectable increments, but, may not be pulled in the opposite direction. When the ratchet release element 280 is placed in a disengaged position, the end thereof is no longer in communication with the pawl 270—thus, the pulley 260 may be rotated in either direction, and lanyard 240 may be withdrawn from either the lanyard entry aperture 220 or the lanyard exit aperture 230 respectively. In this particular embodiment of the present invention, the ratchet release element 280 is maintained in communication with the pawl 270 by a spring (not shown) until the ratchet release element is manually moved to the disengaged position. In another embodiment of the present invention, the ratchet mechanism may be reversible, thus providing a ratcheting function in both directions. Consequently, in such an embodiment, the lanyard 240 would ratchet through the body portion 110 in one direction or the other, rather than ratcheting in one direction and moving freely in the other.

Although not essential, the end of the lanyard 240 extending from the lanyard entry aperture 220 is preferably equipped with a connector 310. The connector 310 is provided for releasably attaching the lanyard 240 to the cap or other component located at the distal end of the liner that is placed over the residual leg 30. Preferably, the connector 310 allows the lanyard 240 to pass therethrough, so that a knot may then be placed in the end of the lanyard 240 to prevent the removal of the connector 310 therefrom. Preferably, the connector 310 is externally threaded, and is designed to engage a like threaded hole in the cap of the liner. Other means of attachment may also be possible, however, such as, for example, a hook, a pin and loop, or numerous other fastening means. In an alternate embodiment, the end of the lanyard 240 may simply be tied to a cleat or similar element provided on the cap of the liner. The connector 310 preferably has an outside diameter that makes it difficult, if not impossible, to pull the connector through the lanyard passageway formed by the lanyard aperture 200 and suction cup receiving aperture 170.

As described infra, one problem associated with a tight fitting prosthesis is the expulsion of air therefrom during the fitting of the prosthesis to the residual limb. Because of the tight fit, air that becomes trapped in the receiving cavity 60 of the prosthetic leg 20 during insertion of the residual leg 30, may be forced out from any gaps. The escape of this air may often be accompanied by rather embarrassing sounds. To alleviate this problem, the system of the present invention forces any trapped air in the upper portion 40 of the prosthetic leg 20 to exit via a single exhaust passageway 320, and preferably through a one-way valve 330. The exhaust passageway 320 is provided through the cup-shaped portion of the distal adapter 140. A corresponding aperture is located through the bottom of the upper portion 40 of the prosthetic leg 20. The trapped air travels through the exhaust passageway 320, through the aperture in the bottom of the upper portion 40 of the prosthetic leg 20, and into an exhaust port 340 located in the body portion 110. The exhaust port 340 then directs the trapped air through a one-way valve 330 that resides within the body portion 110. In this embodiment, the one-way valve 330 consists of an umbrella valve, however, other one-way valves may also be employed with satisfactory results, such as, for example, a duck-bill valve. The one way valve 330 prevents any air from traveling back toward the receiving cavity 60 through the exhaust port 340 and exhaust passageway 320. A muffler 350 may also be provided in or on the body portion 110 to quiet the escaping air as it passes through the one-way valve 330. In this particular embodiment, the muffler 350 is comprised of a porous filter, although other types of mufflers may also be utilized. Preferably, the muffler 350 is located in or on the body portion 110 in line with the one-way valve 330.

In order to ensure that any trapped air exits the upper portion 40 of the prosthetic leg 20, o-rings or other sealing devices are preferably employed at various locations. As can be seen, in this embodiment, a first set of o-rings 370 is employed around the outer circumference of the distal adapter 140. The first set of o-rings 370 are designed to provide a seal with the inside surface of the upper portion 40 of the prosthetic leg 20. The seal produced by the first set of o-rings 370 helps to ensure that no trapped air escapes from the bottom of the upper portion 40 by way of gaps that may exist around the outer circumference of the distal adapter 140. When the upper portion 40 of the prosthetic leg 20 is of a laminated construction, the o-rings 370 may be unnecessary, as the distal adapter 140 will likely be laminated directly to the upper portion. The first end 180 of the suction cup 150 is also adapted to provide a seal with the suction cup receiving aperture 170, such that no trapped air can escape through the center of the distal adapter 140. A second set of o-rings 380 is shown to be provided around the outer circumference of the connector 310. The second set of o-rings 380 provides for a seal between the connector 310 and the lanyard aperture 200 in the suction cup 150, such that no trapped air can exit the upper portion 40 of the prosthetic leg 20 via the lanyard passageway. A third set of o-rings 390 is shown to be provided on either side of the exhaust port 340. The third set of o-rings 390 helps to assure that the trapped air exiting through the exhaust port 340 will be forced through the one-way valve 330 and optional muffler 350, and will not be allowed to escape within or along the top surface of the body portion 110.

In use, the system and method of the present invention depicted in FIGS. 1–3 provides for a more secure and easy to use means of retention for a prosthetic leg. To use the embodiment of the present invention shown in FIGS. 1–3, the amputee 10 first places a liner over the residual leg 30 that will be attached to the prosthetic leg 20. The liner preferably has a cap or cup at the distal end thereof, with a means for attaching the lanyard 240 provided thereon. As discussed above, attachment of the lanyard 240 may be accomplished by various means, but in this example will be described using the connector 310. The connector 310 will already be attached to the end of the lanyard 240 residing within the receiving cavity 60 of the prosthetic leg 20. If not already in the disengaged position, the ratchet release element 280 is set thereto. The connector 310 and lanyard 240 may then be withdrawn from the lanyard entry aperture 220 toward the top of the prosthetic leg 20. Once enough slack is present in the lanyard 240, the connector 310 may be releasably attached to the liner cap. After attachment of the connector 310, the ratchet release element 280 may be returned to the engaged position. The lanyard 240 may then be withdrawn through the lanyard exit aperture 230 so that the slack is removed therefrom. The amputee 10 may then insert the residual leg 30 into the receiving cavity 60. The amputee 10 may insert the residual limb some distance, tighten the lanyard 240, then repeat the process until the distal end of the residual leg 30 is seated against the suction cup 150 and the lanyard is taut. Alternatively, the amputee 10 may provide substantially constant tension on the lanyard 240 as the residual leg 30 is inserted into the receiving cavity 60, thereby assisting with the insertion process and preventing accumulation of slack in the lanyard 240.

The ratchet mechanism 250 allows the lanyard 240 to be tightened in discernible degrees. The ratchet mechanism also prevents the lanyard 240 from slipping back toward the residual leg 30 if tension thereon is relieved or released. Thus, unlike known systems, the system and method of the present invention allows the tension generated by pulling on the lanyard 240 to remain even if the lanyard is released by the amputee 10. This is especially beneficial to those persons who may not possess sufficient strength to maintain constant pressure on the lanyard 240, due to, for example, advanced age or an arthritic condition. To further assist such persons, a detachable handle 400 may be affixed to the free end of the lanyard 240 to provide for a better grip. Once the distal end of the residual leg 30 is seated against the suction cup 150, a vacuum is typically formed therebetween. The tension force of the lanyard 240 assists the vacuum of the suction cup 150 in maintaining the fully inserted position of the residual leg 30 in the receiving cavity 60. Because the taut state of the lanyard 240 is maintained by the ratchet mechanism 250, the slack, free end of the lanyard may then simply be releasably affixed to a feature (not shown), such as a belaying cleat, a hook, or multitude of other features preferably provided on the upper portion 40 of the prosthetic leg 20. While not essential to the present invention, providing a releasable means of attachment for the free end of the lanyard 240 is preferable in order to keep it out of the way. During the installation process, any air trapped in the upper portion 40 of the prosthetic leg 20 is expelled therefrom through the provided muffler 330.

To remove the prosthetic leg 20 using the embodiment of the present invention depicted in FIGS. 1–3, the amputee 10 simply releases the free end of the lanyard 240 and moves the ratchet release mechanism 280 to the disengaged position. The lanyard 240 may then be freely pulled through the body portion 110 in either direction. In an alternate embodiment, wherein the ratchet mechanism is reversible rather than releasable, the ratcheting function is reversed, and the lanyard 240 may be ratcheted in a direction that allows the residual leg 30 to be removed from the receiving cavity 60. Thus, with either embodiment, as the residual leg 30 is withdrawn from the receiving cavity 60, the connector 310 and lanyard 240 will be withdrawn therewith through the lanyard entry aperture 220. Upon withdrawal of the residual leg 30, the connector 310 can be detached from the liner, thereby freeing the residual leg from the prosthetic leg 20.

The ratchet mechanism 250 is merely one example of an adjustable retention mechanism that may be used in the present invention. Various other similar, suitable, or conventional retention mechanisms may be substituted for the ratchet mechanism 250. The adjustability of the retention mechanism may be incremental. Examples of other suitable retention mechanisms that may be used in the present invention include a spring-loaded cleat, a cam mechanism, or other similar types of mechanisms. The type of retention mechanism may be selected to suit the particular type of lanyard 240 and to provide the desired degree of adjustability.

Figure 4:
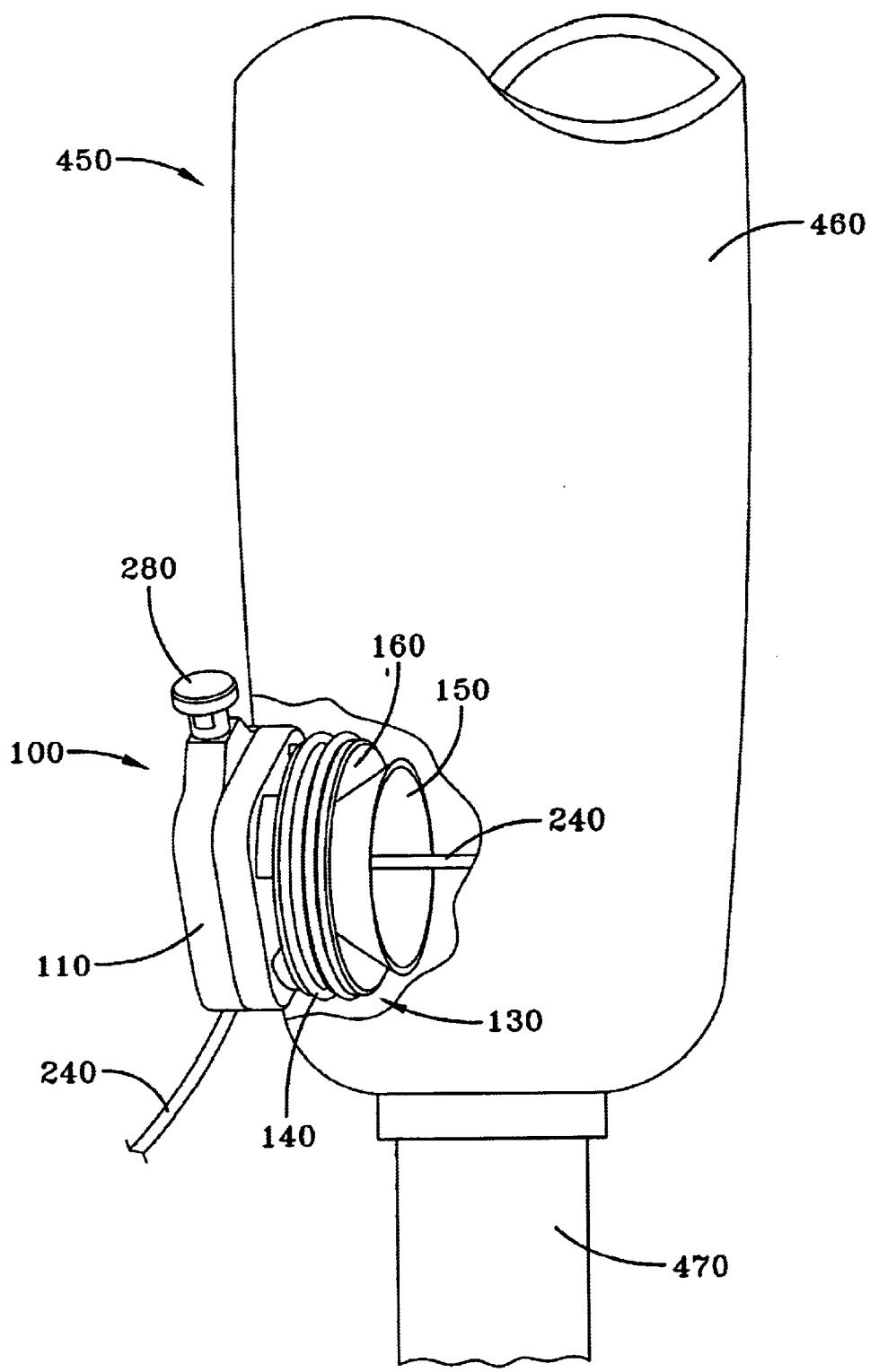
FIG. 4 illustrates an alternate embodiment of the present invention.
Figure 5A:
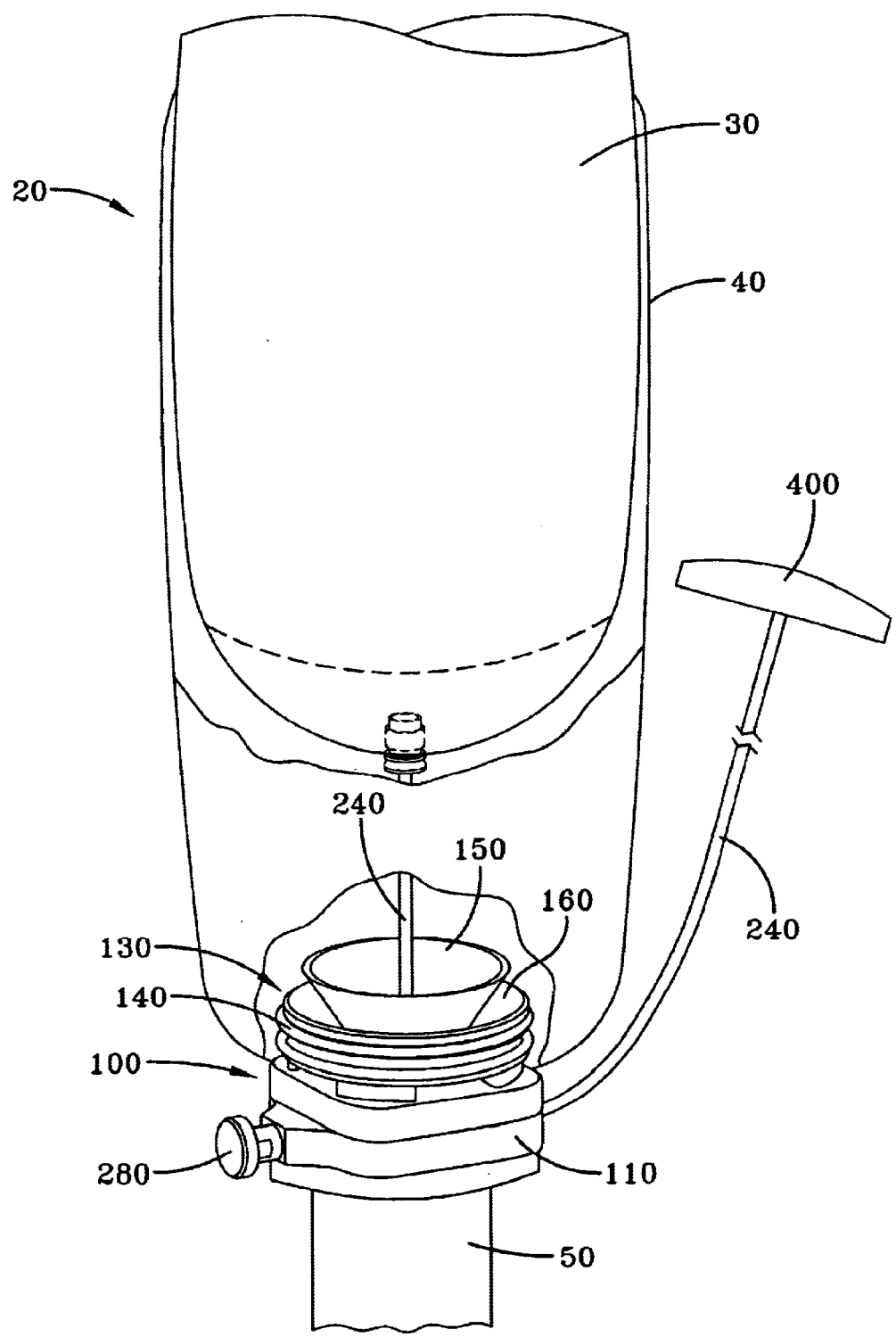
FIG. 5a depicts one embodiment of a liner-covered residual limb being drawn into the prosthetic leg of FIG. 2 by an attached lanyard.
Figure 5B:
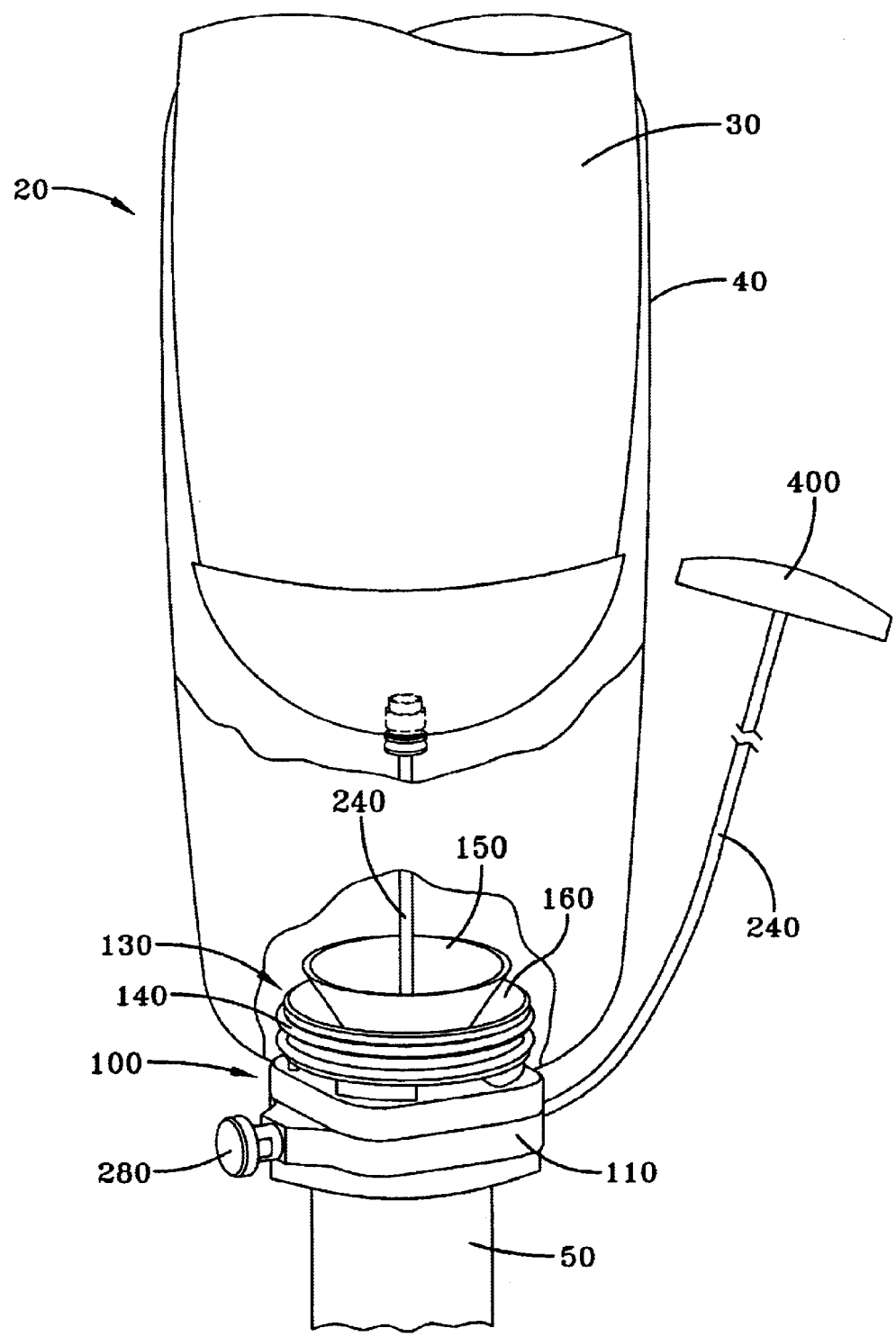
FIG. 5b depicts an alternate embodiment of a liner-covered residual limb being drawn into the prosthetic leg of FIG. 2 by an attached lanyard.

An alternate embodiment of the present invention is depicted in FIG. 4. This embodiment of the present invention is similar to the embodiment illustrated in FIGS. 1–3, except that the ratchet retention apparatus 100 is mounted to the side of the upper portion 460 of a prosthetic leg 450; as opposed to between the upper portion and a lower portion 470 thereof. In this embodiment, the residual leg 30 is again covered with a liner of a construction as described above. The connector 310 is attached to the end of the lanyard 240 and to an attachment element on the liner. However, rather than attaching to the bottom of the distal end of the liner, the connector 310 is attached to a side of the cap located on the distal end of the liner. Thus, in this embodiment 450, the lanyard 240 can still be used to draw the residual leg 30 into the receiving cavity 60 and to secure the position of the residual leg therein. The difference between this embodiment and the embodiment of FIGS. 1–3 is that the tensional force exerted on the residual limb 30 by the lanyard 240 is at an angle rather than substantially directly downward.

Variations of the embodiment of the present invention shown in FIG. 4 are also possible. For example, the ratchet retention apparatus 100 may be mounted at virtually any location on the side of the upper portion 40 of the prosthetic leg 20. As the residual limb 30 is secured to the side of the receiving cavity 60 in such an embodiment, the ratchet retention mechanism 100 does not have to be located near the bottom of the receiving cavity. Similarly, the lanyard 240 may be attached to the liner at various locations other than at the distal end thereof. Consequently, modified versions of the above-described liner may be employed. Additionally, the distal adapter 140 and suction cup 150 may not be used in such an embodiment. Rather, it may be desired to impart a flush interior surface to the receiving cavity 60 in order to allow for easier insertion of the residual limb 30. Therefore, the lanyard 240 may pull the residual limb 30 directly into contact with the receiving cavity 60, rather than into contact with a residual limb receiving device.

As can be seen from the foregoing, the system and method of the present invention provides for an easy to use means of securing a residual limb to a prosthetic limb. The ratcheting function of the system and method of the present invention may be used by persons who may not have the strength to use known lanyard securing systems. Further, the ratcheting mechanism essentially locks the lanyard into position, thereby eliminating the possibility that the tension exerted on the residual limb thereby may be lost or compromised during installation of the prosthetic limb or securing of the lanyard. The ratcheting function of the present invention also effectively provides for a more secure retention of the prosthetic limb on the residual limb because the tension of the lanyard remains constant, thereby ensuring that the abutting relationship of the distal end of the residual limb to the suction cup is maintained. Consequently, aside from the fact that the present invention is easier to use than known systems, the present invention can also minimize or even eliminate the pistoning phenomenon previously described.

While exemplary embodiments of the system and method of the present invention have been described in detail above only with respect to a prosthetic leg, it should be realized by one skilled in the art that the system and method may also be employed with other prostheses. Thus, while certain embodiments of the present invention are described in detail above, the scope of the invention is not to be considered limited by such disclosure, and modifications are possible without departing from the spirit of the invention as evidenced by the following claims:

What is claimed is:

1. A system for releasably securing a prosthetic limb to a residual limb, comprising:

a liner for fitting over said residual limb, said liner having a distal end that is adapted to mate with a receiving device located in a receiving cavity of a first portion of said prosthetic limb, said distal end further having a connecting means for permitting releasable connection of said liner to a lanyard;

a receiving device located near a bottom of said receiving cavity, said receiving device provided to mate with said distal end of said liner and to produce an evacuated seal therewith;

a releasable retention mechanism affixed between said first portion of said prosthetic limb and a second portion of said prosthetic limb;

a passageway leading from said receiving cavity in said first portion of said prosthetic limb, through said receiving device, and into said retention mechanism; and a lanyard running from said receiving cavity through said passageway and said retention mechanism, said lanyard having a first end located in said receiving cavity for releasable attachment to said connecting means on said distal end of said liner, and a second, free end, located outside said prosthetic limb;

wherein during donning of said prosthetic limb, said residual limb is drawn into said receiving cavity as said lanyard is pulled through said retention mechanism by a user of said system, and is held against withdrawal from said receiving cavity at any position therein due to gripping of said lanyard by said retention mechanism; and wherein said prosthetic limb is configured to be retained on said residual limb during use by a combination of said evacuated seal and tension in said lanyard.

2. The system of claim 1, wherein said distal end of said liner has a cap attached thereto.

3. The system of claim 1, further comprising a suction cup attached to said receiving device, said suction cup adapted to receive a distal end of said residual limb.

4. The system of claim 1, wherein said retention mechanism is a ratchet mechanism that provides a ratcheting function in only one direction.

5. The system of claim 1, wherein said retention mechanism is a ratchet mechanism that provides a ratcheting function in both directions.

6. The system of claim 1, further comprising a connector affixed to said first end of said lanyard, said connector for releasably connecting said lanyard to said connecting means on said distal end of said liner.

7. The system of claim 1, further comprising a handle affixed to said as second end of said lanyard.

8. The system of claim 1, further comprising a holding device attached to the outside of said prosthetic leg for releasably maintaining the free end of said lanyard.

9. The system of claim 1, further comprising a passageway for exhausting any trapped air from said receiving cavity to the outside atmosphere.

10. The system of claim 9, further comprising a one-way valve located in line with said passageway, said one-way valve for prohibiting the flow of air from said outside atmosphere into said receiving cavity.

11. The system of claim 10, further comprising a muffler located in line with said one-way valve for muffling the sound of said trapped air as said trapped air is exhausted from said receiving cavity.

12. The system of claim 1, wherein said receiving device is integral to said first portion of said prosthetic limb.

13. A system for releasably securing a prosthetic leg to a residual leg, said prosthetic leg having a substantially hollow upper portion and a lower portion, said system comprising:

a liner for placement over said residual leg, a distal end of said liner adapted for attachment to a lanyard and further adapted to mate with a residual leg receiving device located in said upper portion of said prosthetic leg;

a residual leg receiving device located near the bottom of said substantially hollow portion of said prosthetic leg, said residual leg receiving device having a suction cup for mating with said distal end of said liner;

a passageway leading through said suction cup, said residual leg receiving device, and said upper portion of said prosthetic leg;

a releasable ratchet mechanism affixed to said upper portion of said prosthetic leg between a bottom of said upper portion and the top of said lower portion;

a pathway leading through said ratchet mechanism, such that a first end of said pathway is in communication with said passageway leading through said residual leg receiving device and said upper portion of said prosthetic leg, and a second end exits to the outside of said prosthetic leg; and a lanyard running from within said substantially hollow upper portion through said residual leg receiving device and said ratchet mechanism, said lanyard having a first end located in said upper portion and adapted for attachment to said liner, and a second, free end, located outside said prosthetic leg;

whereby, once said lanyard is connected to said liner, pulling on said second end of said lanyard draws a distal end of said residual leg toward said bottom of said substantially hollow upper portion of said prosthetic leg, while said ratchet mechanism prevents movement of said lanyard in an opposite direction.

14. The system of claim 13, further comprising a connector affixed to said first end of said lanyard, said connector for attaching said lanyard to said liner.

15. The system of claim 13, further comprising a handle affixed to said second end of said lanyard.

16. The system of claim 13, further comprising a holding device attached to the outside of said prosthetic leg for releasably maintaining the free end of said lanyard.

17. The system of claim 13, further comprising a passageway for exhausting any air trapped within said upper portion of said prosthetic leg to the outside atmosphere.

18. The system of claim 17, further comprising a one-way valve located in line with said passageway, said one-way valve for prohibiting the flow of air from said outside atmosphere into said upper portion of said prosthetic leg.

19. The system of claim 18, further comprising a muffler located in line with said one-way valve for muffling the sound of said trapped air as said trapped air is exhausted from said upper portion of said prosthetic leg.

20. A method of releasably securing a residual limb to a prosthetic limb, said method comprising:

providing a liner for placement over at least a portion of said residual limb, a distal end of said liner adapted to mate with a residual limb receiving device and having a connecting means for permitting releasable connection to a first end of a lanyard;

providing a prosthetic limb having a first portion with a receiving cavity located therein, and a second portion connected to said first portion;

locating a residual limb receiving device to said prosthetic limb such that at least a portion of said residual limb receiving device resides within said receiving cavity and near a bottom portion thereof, said receiving device producing an evacuated seal with said distal end of said liner when in contact therewith;

providing a ratcheting mechanism near a distal end of said first portion of said prosthetic limb;

providing a lanyard that passes through said ratcheting mechanism and said residual limb receiving device, a first end of said lanyard exiting said receiving device into said receiving cavity and a second end of said lanyard exiting from said ratcheting mechanism to the outside of said prosthetic limb;

placing said liner over at least a distal end of said residual limb;

releasably connecting said first end of said lanyard to said connecting means on said distal end of said liner;

inserting said residual limb into said receiving cavity; and placing tension on said second end of said lanyard, thereby encouraging said distal end of said residual limb toward said bottom portion of said receiving cavity and into evacuated engagement with said residual limb receiving device;

whereby as tension is placed on said second end of said lanyard, said ratchet mechanism grips said lanyard and resists movement of said residual limb in a direction away from said bottom of said receiving cavity, regardless of the position of said residual limb with respect to said receiving cavity; and wherein said prosthetic limb is retained on said residual limb during use by a combination of said evacuated seal and tension retained in said lanyard.

21. The method of claim 20, further comprising securing the second end of said lanyard to a securing device located on the outside of said prosthetic limb after said prosthetic limb is secured to said residual limb.

22. The system of claim 1, wherein said releasable retention mechanism is selected from the group consisting of ratcheting mechanisms, cam mechanisms, and spring-loaded cleats.

23. The method of claim 20, further comprising disengaging said ratchet mechanism before removing said prosthetic limb.

24. The method of claim 20, further comprising providing a handle at the second end of said lanyard.

25. The method of claim 20, further comprising providing an exhaust passageway for allowing air trapped in said receiving cavity to escape to the outside atmosphere.

26. The method of claim 25, further comprising providing a one-way valve in said exhaust passageway.

27. The method of claim 25, further comprising providing a muffler in said exhaust passageway.

28. The method of claim 25, further comprising providing seals for ensuring that said trapped air is forced to exit said receiving cavity through said exhaust passageway.

29. The method of claim 20, further comprising providing a connector affixed to said first end of said lanyard for releasably attaching said lanyard to said liner.

30. A system for releasably securing a prosthetic limb to a residual limb, comprising:

a liner for covering at least a distal end of said residual limb, the distal end of said liner having a cap attached thereto, said cap adapted to mate with a residual limb receiving device that enters a residual limb receiving cavity formed in said prosthetic limb near a distal end thereof, said cap further having a connector for allowing releasable connection to a lanyard;

a releasable ratchet mechanism affixed to said prosthetic limb near said distal end of said residual limb receiving cavity;

a passageway leading from within said residual limb receiving cavity through said residual limb receiving device and into said releasable ratchet mechanism; and a lanyard running from within said residual limb receiving cavity, through said passageway, and through a convoluted path within said ratchet mechanism, said lanyard having a first end provided with a connector for releasable attachment to said connector on said cap, and a second, free end, located outside said prosthetic limb;

whereby placing tension on said free end of said lanyard encourages said distal end of said residual limb toward said bottom of a residual limb receiving cavity and into mating contact with said residual limb receiving device, while, at any position of said residual limb with respect to said receiving cavity, said ratchet mechanism prevents movement of said lanyard and said residual limb connected thereto in an opposite direction.

31. The system of claim 30, wherein said releasable ratchet mechanism is located beneath said residual limb receiving cavity.

32. The system of claim 30, wherein said releasable ratchet mechanism is located on a side of a first portion of said prosthetic limb, near the distal end thereof.

* * * * *

UNITED STATES PATENT AND TRADEMARK OFFICE
CERTIFICATE OF CORRECTION

PATENT NO. : 6,797,008 B1  
APPLICATION NO. : 10/033064  
DATED : September 28, 2004  
INVENTOR(S) : Robert E. Arbogast et al.

It is certified that error appears in the above-identified patent and that said Letters Patent is hereby corrected as shown below:

Column 6  
Line 66, please delete the "comma" between the words "but" and "may".

Column 11  
Line 66, please delete the word "the" and replace it with -- a --.

Column 12  
Line 7, please delete the word "a" and replace it with -- the --.

Column 14  
Line 30, please delete the word "said" and replace it with -- a --.  
Line 30, please delete the word "a" and replace it with -- said --.  
Line 41, please delete the word "the" and replace it with -- a --.

Signed and Sealed this

Fifth Day of August, 2008

JON W. DUDAS  
*Director of the United States Patent and Trademark Office*